(12) United States Patent
Drapkin (10) Patent No.: US 11,039,801 B2
(45) Date of Patent: Jun. 22, 2021

(54) SYSTEMS AND METHODS FOR HIGH-RESOLUTION SPECTRAL COMPUTED TOMOGRAPHY IMAGING

(71) Applicant: GE Precision Healthcare LLC, Milwaukee, WI (US)

(72) Inventor: Evgeny Drapkin, Delafield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 175 days.

(21) Appl. No.: 16/460,748

(22) Filed: Jul. 2, 2019

(65) Prior Publication Data

US 2021/0000434 A1 Jan. 7, 2021

(51) Int. Cl.
*A61B 6/00* (2006.01)
*A61B 6/03* (2006.01)
*G06T 11/00* (2006.01)

(52) U.S. Cl.
CPC ............ *A61B 6/4266* (2013.01); *A61B 6/032* (2013.01); *A61B 6/4241* (2013.01); *A61B 6/5205* (2013.01); *G06T 11/005* (2013.01); *G06T 2211/408* (2013.01); *G06T 2211/421* (2013.01); *G06T 2211/424* (2013.01)

(58) Field of Classification Search
CPC ......... G01T 7/005; G01T 7/02; G01N 21/274; G06T 2211/40; G06T 2211/00; G06T 2211/412; A61B 6/4241; A61B 6/425; A61B 6/4275; A61B 6/4417; A61B 6/5229; A61B 6/5211; A61B 6/5241; A61N 5/1048; G09G 5/00
See application file for complete search history.

(56) References Cited

U.S. PATENT DOCUMENTS

| | | | |
|---|---|---|---|
| 6,963,631 | B2 | 11/2005 | Brunnett |
| 7,362,847 | B2 | 4/2008 | Bijjani |
| 8,488,854 | B2 | 7/2013 | Arenson et al. |
| 8,965,095 | B2 | 2/2015 | Zou et al. |
| 9,262,845 | B2 | 2/2016 | Carmi et al. |
| 9,310,495 | B2 | 4/2016 | Spartiotis et al. |
| 2013/0214144 | A1* | 8/2013 | Hannemann ........... A61B 6/585 250/252.1 |
| 2014/0037045 | A1 | 2/2014 | Dafni et al. |

\* cited by examiner

*Primary Examiner* — Don K Wong
(74) *Attorney, Agent, or Firm* — McCoy Russell LLP (57) ABSTRACT

Methods and systems are provided for high-resolution computed tomography imaging. In one embodiment, a method comprises detecting, with a detector array comprising a plurality of individual detectors each configured with a first number of energy bins, photons generated by an x-ray source and attenuated by a subject to be imaged, generating a first dataset, for a virtual detector array comprising a combination of individual detectors and macro-detectors, by selectively aggregating a subset of the individual detectors into the macro-detectors with a second number of energy bins, generating a second dataset, for an augmented detector array comprising the plurality of individual detectors each configured with the second number of energy bins, by up-sampling the first dataset, and reconstructing an image of the subject from the second dataset. In this way, high-resolution detector arrays can acquire minimal data while maintaining a high image resolution and spectral resolution.

20 Claims, 5 Drawing Sheets

SYSTEMS AND METHODS FOR HIGH-RESOLUTION SPECTRAL COMPUTED TOMOGRAPHY IMAGING

FIELD

Embodiments of the subject matter disclosed herein relate to non-invasive diagnostic imaging, and more particularly, to high-resolution spectral computed tomography imaging.

BACKGROUND

Dual or multi-energy spectral computed tomography (CT) systems can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of CT, two physical processes dominate the x-ray attenuation: Compton scattering and the photoelectric effect. The detected signals from two energy regions provide sufficient information to resolve the energy dependence of the material being imaged. Detected signals from the two energy regions provide sufficient information to determine the relative composition of an object composed of two hypothetical materials.

BRIEF DESCRIPTION

In one embodiment, a method comprises detecting, with a detector array comprising a plurality of individual detectors each configured with a first number of energy bins, photons generated by an x-ray source and attenuated by a subject to be imaged, generating a first dataset, for a virtual detector array comprising a combination of individual detectors and macro-detectors, by selectively aggregating a subset of the individual detectors into the macro-detectors with a second number of energy bins, generating a second dataset, for an augmented detector array comprising the plurality of individual detectors each configured with the second number of energy bins, by up-sampling the first dataset, and reconstructing an image of the subject from the second dataset. In this way, high-resolution detector arrays can acquire minimal data while maintaining a high image resolution and spectral resolution, thereby improving efficiency of data transfer when bandwidth is limited.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
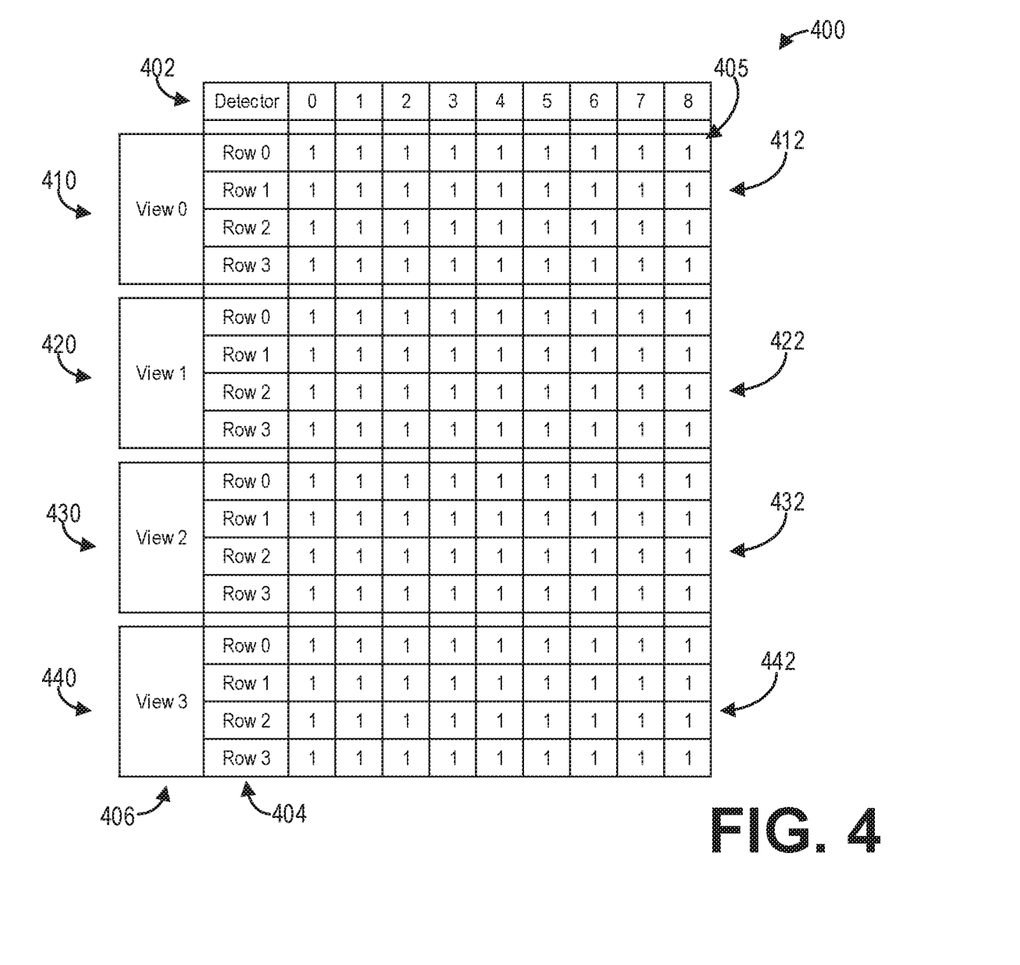
FIG. 4 shows a table illustrating an example distribution of energy bins among individual detectors in a detector array for a sequence of views according to an embodiment.
Figure 5:
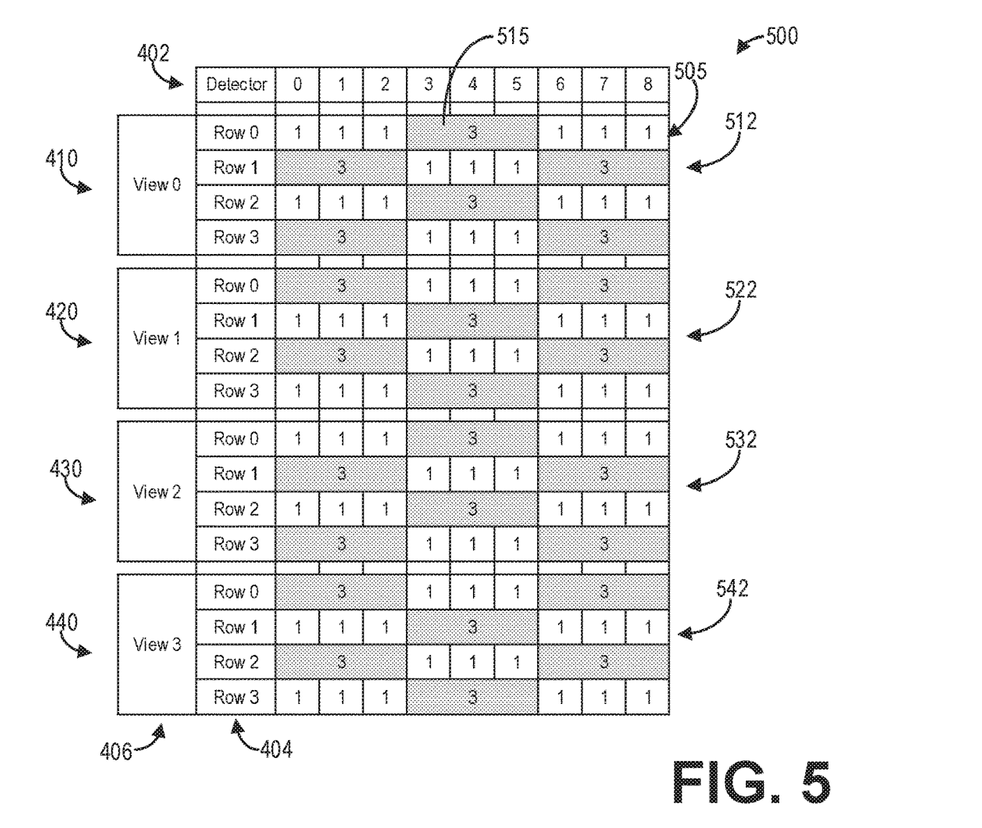
FIG. 5 shows a table illustrating an example distribution of energy bins among individual detectors and macro-detectors in a detector array for a sequence of views according to an embodiment.
Figure 6:
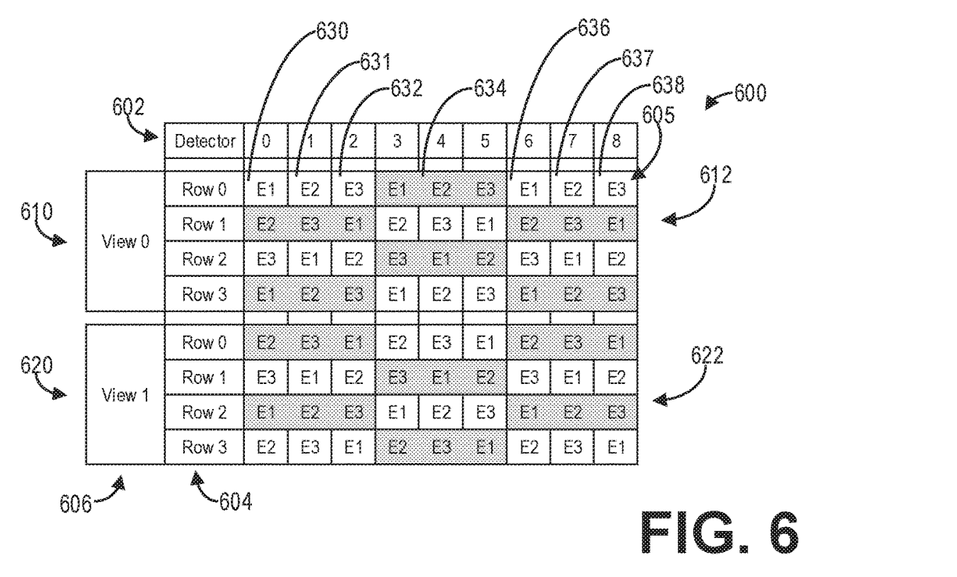
FIG. 6 shows a table illustrating an example distribution of energy bins for different energy levels among individual detectors and macro-detectors in a detector array for a sequence of views according to an embodiment.
Figure 7:
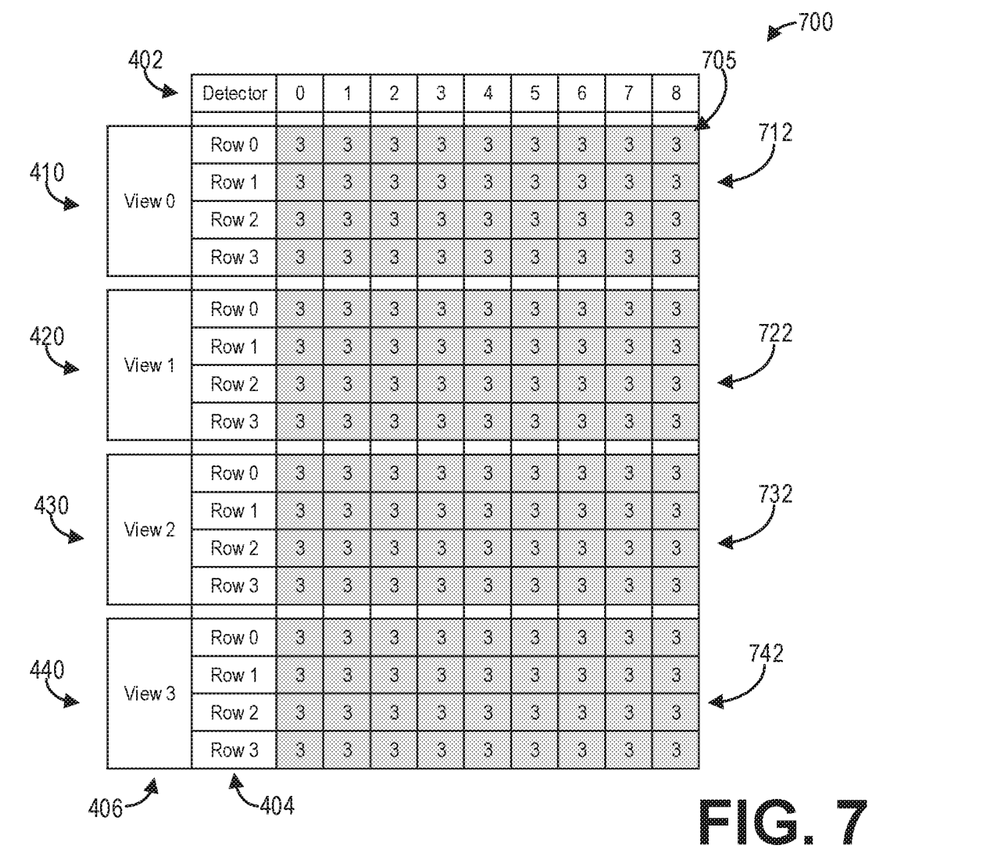
FIG. 7 shows a table illustrating an example distribution of energy bins among individual detectors in a detector array for a sequence of views after up-sampling according to an embodiment.

The following description relates to various embodiments of medical imaging systems. In particular, systems and methods are provided for computed tomography imaging with high-resolution detector arrays. An example of a CT imaging system that may be used to acquire images in accordance with the present techniques is provided in FIGS. 1 and 2. The CT imaging system may include a high-resolution detector array with a large plurality of individual detectors arranged in detector rows. For spectral CT imaging with various photon energies, such as dual energy CT imaging, the total amount of data collected during a scan may be extremely large, which may necessitate relatively high-bandwidth slip rings and large data buffers for transmitting the data from the CT gantry during the scan. A method for spectral CT imaging with high-resolution detector arrays, such as the method depicted in FIG. 3, includes selectively aggregating data from individual detectors with a first number of energy bins into macro-detectors with a second number of energy bins larger than the first number, thereby producing a dataset with a reduced file size, and up-sampling the dataset after the dataset is transmitted from the rotating gantry. The detector array may be configured such that each individual detector detects photons with the first number of energy bins, as depicted in FIG. 4. The data acquisition system of the imaging system may then selectively aggregate data from individual detectors into macro-detectors with the second number of energy bins, as depicted in FIG. 5, in an alternating pattern throughout the detector array as well as throughout different views. Further, the data acquisition system may alternate the distribution of energy bins throughout the detector array between detector rows and between views to further minimize information loss, as depicted in FIG. 6. By selectively alternating the individual detectors and the macro-detectors, the data may be up-sampled into a full dataset corresponding to a high-resolution detector array wherein each detector is configured with the second number of energy bins, as depicted in FIG. 7, throughout all views. The systems and methods provided herein thus enable the sparse acquisition of raw spectral CT data while preserving a high resolution. In this way, the size of an acquired dataset may be substantially reduced, with minimal information loss for resolution and spectral energy information, thereby enabling the use of high-resolution detector arrays with a large number of energy bins for imaging systems with limited bandwidth for transmitting data during an imaging scan, for example via a slip ring or wireless transmission. As an example, the methods described herein enable the reduction of a file size of a dataset by as much as two or three times with minimal information loss for resolution and energy information. Further, the method of selectively aggregating photon counts during data acquisition as described further herein enables the dataset to be up-sampled to a resolution substantially higher than the resolution of the initially detected data.

Though a CT system is described by way of example, it should be understood that the present techniques may also be useful when applied to images acquired using other imaging modalities, such as tomosynthesis, MM, C-arm angiography, and so forth. The present discussion of a CT imaging modality is provided merely as an example of one suitable imaging modality.

Figure 1:
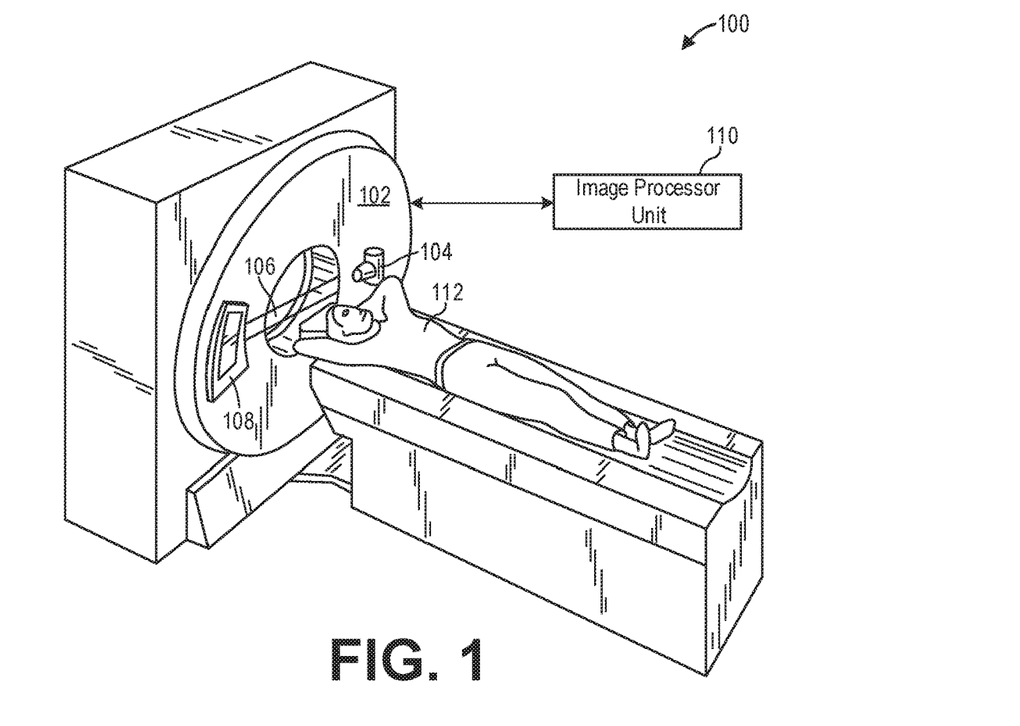
FIG. 1 shows a pictorial view of an imaging system according to an embodiment.

FIG. 1 illustrates an exemplary CT system 100 configured for dual energy imaging with automatic tube potential selection. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources and detectors may be employed to project a plurality of x-rays 106 for acquiring projection data corresponding to the patient at different energy levels. In some embodiments, the x-ray radiation source 104 may enable dual-energy gemstone spectral imaging (GSI) by rapid kVp switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some known CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

The projection data is processed to reconstruct an image that corresponds to a two-dimensional slice taken through the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
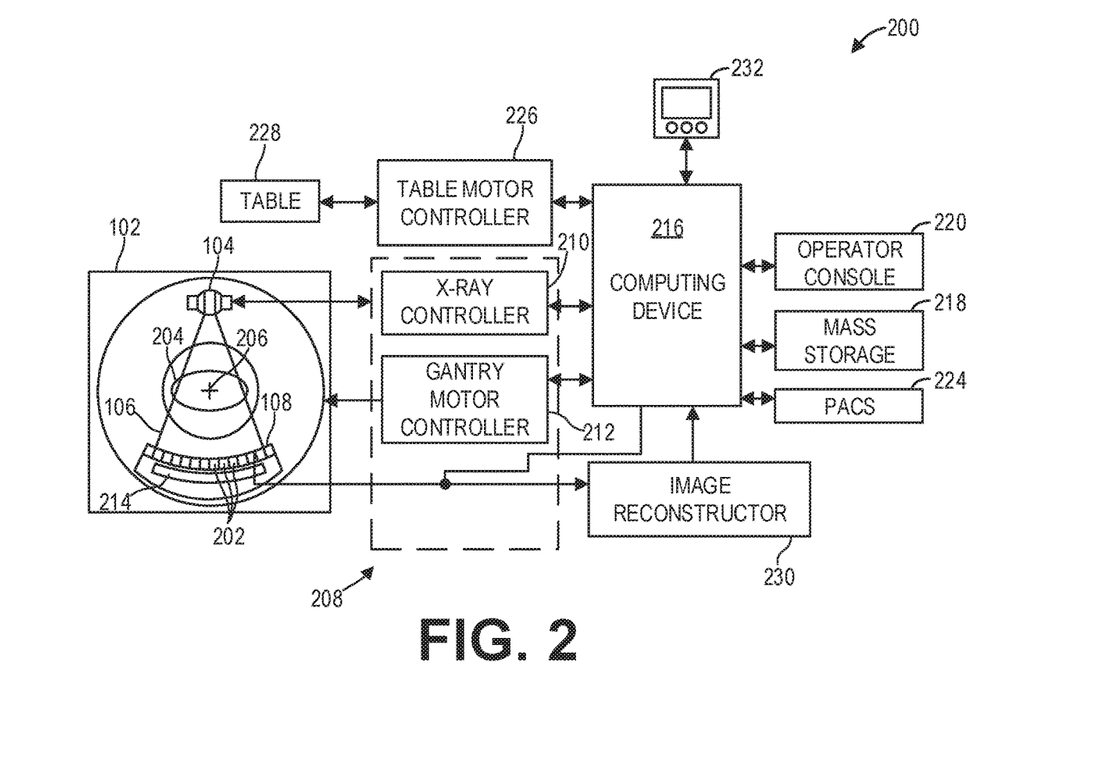
FIG. 2 shows a block schematic diagram of an exemplary imaging system according to an embodiment.

FIG. 2 illustrates an exemplary imaging system 200 similar to the CT system 100 of FIG. 1. In accordance with aspects of the present disclosure, the imaging system 200 is configured for dual energy imaging with automatic selection of tube potentials. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may comprise photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
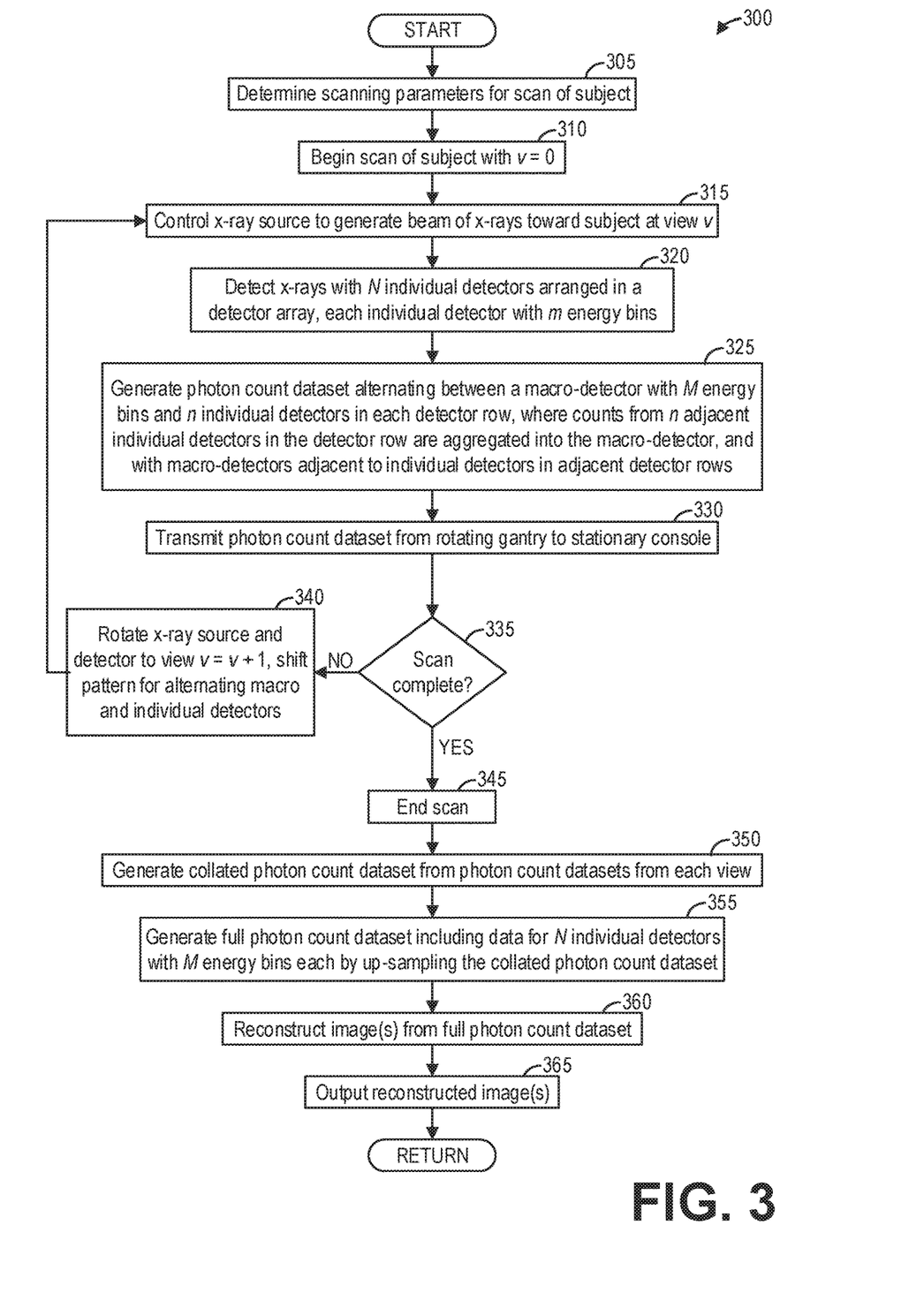
FIG. 3 shows a high-level flow chart illustrating an example method for multi-energy imaging with robust data compression during acquisition according to an embodiment.

FIG. 3 shows a high-level flow chart illustrating an example method 300 for multi-energy imaging with increased image resolution according to an embodiment. Method 300 is described with regard to the systems and components of FIGS. 1 and 2, though it should be appreciated that the method 300 may be implemented with other systems and components without departing from the scope of the present disclosure. Method 300 may be implemented as executable instructions in non-transitory memory of one or more computing devices, such as the image reconstructor 230 and/or the computing device 216.

Method 300 begins at 305. At 305, method 300 determines scanning parameters for a scan of a subject. The scanning parameters may comprise one or more parameters for controlling the x-ray source 104, the detector array 108, the DAS 214, the gantry 102, and/or the table 228, for example, to image a desired region of interest of the subject 204. To that end, the scanning parameters may include one or more of a scan range, a target dose, helical pitch, two or more tube currents, two or more tube potentials, and so on. One or more of the scanning parameters may be tailored to the subject being scanned. Method 300 determines two or more tube currents and/or two or more tube potentials such that the subject 204 may be imaged at different energy levels, for example using dual or multi-energy imaging techniques.

At 310, method 300 begins the scan of the subject at a view v=0. To that end, method 300 may adjust a position of the gantry 102 via the gantry motor controller 212 such that the x-ray source 104 and the detector array 108 are in an initial position relative to the subject 204 corresponding to an initial view or zeroth view v=0.

At 315, method 300 controls the x-ray source to generate a beam of x-rays toward the source at the view v. For example, method 300 may control the x-ray source 104 with at least two tube potentials and at least two tube currents to generate a plurality of x-rays 106 including x-rays with a first energy level and x-rays with a second energy level, wherein the first energy level and the second energy level of the x-rays are determined by the at least two tube potentials. For example, method 300 may switch between the tube potentials and the tube currents to generate different beams of x-rays with different energy levels. In other examples, method 300 may control a first x-ray source such as the x-ray source 104 with a first tube potential and a first tube current to generate x-rays with a first energy level, and a second x-ray source with a second tube potential and a second tube current to generate x-rays with a second energy level. It should be appreciated that x-rays or various energy levels may be generated according to other dual or multi-energy imaging techniques without departing from the scope of the present disclosure.

At 320, method 300 detects x-rays with N individual detectors arranged in a detector array, each individual detector with m energy bins. The individual detectors may comprise photon-counting detectors which register the interactions of individual photons. As an example, when a photon such as an x-ray attenuated by the subject interacts with an individual detector of the detector array, the individual detector generates a corresponding electrical pulse proportional to the energy of the photon. Each energy bin of the m energy bins of an individual detector comprises an energy range, such that if the energy of the photon is within the energy range of an energy bin of the m energy bins, the individual detector counts the photon within the energy bin.

At 325, method 300 generates a photon count dataset alternating between a macro-detector with M energy bins and n individual detectors in each detector row, where counts from n individual detectors in the detector row are aggregated into the macro-detector, and with macro-detectors adjacent to individual detectors in adjacent detector rows. That is, method 300 aggregates, via the DAS 214 for example, photon counts from n individual detectors (with m energy bins each) adjacent to each other in a detector row as if a single detector with M energy bins (wherein M equals n times m) were positioned in place of the n individual detectors in the detector array. Thus, the photon count dataset is generated by method 300 as if each detector row of the detector array alternated between n individual detectors and a macro-detector, rather than a plurality of individual detectors. Further, the alternating pattern between individual detectors and macro-detectors is shifted between adjacent detector rows, such that the first n individual detectors in a first detector row are counted in the photon count dataset as n individual detectors with m energy bins each, while the first n individual detectors in a second detector row adjacent to the first detector row are counted in the photon count dataset as a single macro-detector with M energy bins, the first n individual detectors in a third detector row are counted as n individual detectors, and so on throughout the detector array.

After selectively aggregating the photon counts into macro-detectors to generate the photon count dataset, method 300 continues to 330. At 330, method 300 transmits the photon count dataset from the rotating gantry to the stationary console. For example, as the DAS 214 and the detector array 108 are positioned on the gantry 102 which rotates during the scan, the bandwidth between the DAS 214 and the image reconstructor 230 and/or the computing device 216 may be limited by a slip ring enabling data transmission between the rotating components of the imaging system 200 (such as the DAS 214) and stationary components of the imaging system 200 (such as the computing device 216). The photon count dataset for the given view v is therefore transmitted from the rotating components of the imaging system 200 to the stationary components of the imaging system 200 as the dataset is acquired.

Continuing at 335, method 300 determines if the scan is complete. The scan is complete when all views across the desired scan range are acquired. If the scan is not complete ("NO"), method 300 continues to 340. At 340, method 300 rotates the x-ray source and the detector to a view v=v+1, and shifts the pattern for alternating virtual and individual detectors. For example, if the first n individual detectors in a first detector row were aggregated into a macro-detector for the previous view, the same n individual detectors are sampled as individual detectors in the subsequent view. Shifting the alternating pattern between individual detectors and macro-detectors is described further herein with regard to FIG. 5. Furthermore, in some examples, method 300 may shift the energy bins from view to view. For example, assuming two different energy bins are distributed among the individual detectors, an individual detector may be configured to detect photons within a first energy bin for a first view, with a second energy bin for a second view subsequent to the first view, with the first energy bin for a third view subsequent to the second view, and so on. Shifting the distribution of energy bins in this way is described further herein with regard to FIG. 6.

In addition to rotating the gantry to rotate the x-ray source and the detector array, method 300 may adjust the position of the subject by adjusting the position of the table on which the subject is positioned, in some examples. After rotating the gantry to the updated view v and shifting the alternating pattern for individual detectors and macro-detectors, method 300 returns to 315 to acquire an additional photon count dataset at the updated view v. Method 300 thus acquires a photon count dataset for each view v during the scan.

Referring again to 335, once the scan is complete ("YES"), method 300 continues to 345. At 345, method 300 ends the scan. That is, method 300 ceases to control the x-ray source 104 to generate x-rays and to acquire corresponding photon counts via the detector array 108.

Continuing at 350, method 300 generates a collated photon count dataset from the photon count datasets from each view v. It should be appreciated that method 300 may generate the collated photon count dataset from the photon count datasets from each view v as the photon count datasets are received at the stationary console during the scan.

At 355, method 300 generates a full photon count dataset including data for N individual detectors with M energy bins each by up-sampling the collated photon count dataset. For example, method 300 may up-sample the collated photon count dataset using guided bi-linear up-sampling technique or a deep learning-based up-sampling technique into the full photon count dataset. For example, as the distribution of individual detectors with m energy bins and macro-detectors with M energy bins for each view are known, method 300 may perform guided bi-linear up-sampling to generate the full photon count dataset including data for N individual detectors with M energy bins each. As another example, a plurality of test scans may be performed with phantoms or other test subjects, with at least two sets of collated photon count datasets acquired for each test scan, including a collated photon count dataset for a combination detector array including individual detectors with m energy bins and macro-detectors with M energy bins alternating as described herein for the plurality of views v, and a collated photon count dataset acquired with N individual detectors with M energy bins each for the plurality of views v. A deep neural network, for example, may be trained on the collated photon count datasets for the combination detector array as input, with weights of the deep neural network adjusted to reduce the error between the output of the deep neural network and the collated photon count datasets for the full high-resolution detector array. Method 300 may therefore up-sample the collated photon count dataset into the full photon count dataset by inputting the collated photon count dataset generated at 350 into the trained deep neural network.

At 360, method 300 reconstructs one or more images from the full photon count dataset. For example, method 300 may reconstruct one or more images from the full photon count dataset according to dual or multi-energy image reconstruction techniques. As a non-limiting example, method 300 may perform basis material decomposition, reconstruct basis material images, and reconstruct a monochromatic image. It should be appreciated that method 300 may use other spectral CT image reconstruction approaches to reconstruct the one or more images from the full photon count dataset, depending on the number M of energy bins for the full photon count dataset.

At 365, method 300 outputs the reconstructed image(s). For example, method 300 may output the reconstructed image(s) to one or more of a display device 232 for display to an operator, a mass storage 218 for subsequent retrieval and review, or a PACS 224 for remote storage and/or review. Method 300 then returns.

The systems and methods provided herein enable the sparse acquisition of raw spectral CT data while preserving a high resolution. In one sense, the method of selectively aggregating photon counts during data acquisition as described herein enables a substantial reduction in the size of a dataset, with minimal information loss for resolution and spectral energy information, thereby enabling the use of high-resolution detector arrays with a large number of energy bins for imaging systems with limited bandwidth for transmitting data during an imaging scan, for example via a slip ring or wireless transmission. In another sense, the method of selectively aggregating photon counts during data acquisition as described herein enables the dataset to be up-sampled to a resolution substantially higher than the resolution of the initially detected data.

To illustrate the advantages of the systems and methods described herein, FIGS. 4-7 described further herein below depict an illustrative and non-limiting example wherein data from a detector array comprising individual detectors each configured with a single energy bin may be used to obtain a full resolution dataset as if each individual detector were configured with a plurality of energy bins during data acquisition.

FIG. 4 shows a table 400 illustrating an example distribution of energy bins among individual detectors in a detector array 405 for a sequence of views according to an embodiment. Table 400 includes columns corresponding to a plurality of individual detectors 402 as well as rows corresponding to a plurality of detector rows 404. Table 400 further depicts a plurality of views 406, including a zeroth view 410, a first view 420, a second view 430, and a third view 440. Table 400 depicts a distribution of energy bins among the individual detectors of the detector array 405 for each view of the plurality of views 406, including a zeroth distribution 412 for the zeroth view 410, a first distribution 422 for the first view 420, a second distribution 432 for the second view 430, and a third distribution 442 for the third view 440.

In the depicted example, the detector array 405 includes thirty-six individual detectors or detector elements arranged in four detector rows (i.e., row 0, row 1, row 2, and row 3) with nine individual detectors (i.e., detector 0, detector 1, detector 2, detector 3, detector 4, detector 5, detector 6, detector 7, and detector 8) in each detector row. It should be appreciated that the number of detectors and detector rows is illustrative and non-limiting. Further, the zeroth distribution 412 of the energy bins among the detectors includes m energy bins for each individual detector in the detector array 405, where in the depicted example m equals one. Similarly, the first distribution 422, the second distribution 432, and the fourth distribution 442 of the energy bins includes a single energy bin for each individual detector array 405.

It should be appreciated that in some examples, each individual detector may be configured with more than one energy bin. However, the size of the raw data increases linearly as a function of the number of energy bins per detector. For example, the size of the raw data doubles for two energy bins per detector, triples for three energy bins per detector, and so on. For a high-resolution detector with a large number of individual detectors and multiple energy bins per detector, the raw data acquired during a scan may exceed the bandwidth for data transmission between the rotating components of the imaging system 200, such as the DAS 214, and the stationary components of the imaging system 200, such as the image reconstructor 230 and/or the computing device 216.

As discussed hereinabove, photon counts detected by individual detectors may be selectively aggregated into macro-detectors by the DAS during data acquisition. As an illustrative and non-limiting example, FIG. 5 shows a table 500 illustrating an example distribution of energy bins among individual detectors and macro-detectors in a detector array 505 for the sequence of views 406 according to an embodiment. Similar to table 400 of FIG. 4, table 500 includes columns corresponding to the plurality of individual detectors 402 as well as rows corresponding to the plurality of detector rows 404 arranged in a detector array 505. Further, table 500 depicts the plurality of views 406, including the zeroth view 410, the first view 420, the second view 430, and the third view 440.

As described hereinabove, multiple individual detectors with a first number of energy bins (e.g., m energy bins) each may be aggregated into a single "macro-detector" with a second number of energy bins (e.g., M energy bins) greater than the first number of energy bins, wherein the macro-detector comprises a virtual detector spanning the physical space of the multiple individual detectors comprising the macro-detector. For example, n adjacent individual detectors each with m energy bins may be aggregated into a single macro-detector with M energy bins covering the same physical space as then adjacent individual detectors, where M is greater than m. In the example depicted in FIG. 5, for example, the number of individual detectors n aggregated into a macro-detector is three, the first number of energy bins m of the individual detectors is one, and the second number of energy bins M of the macro-detectors is three. In particular, as depicted, three detectors (e.g., detectors 3, 4, and 5 of row 0) in the detector array 505 are aggregated into a single macro-detector 515 with three energy bins, whereas the individual detectors (e.g., detectors 0, 1, 2, 6, 7, and 8 of row 0) in the detector array 505 include one energy bin.

Further, the first three individual detectors (detectors 0, 1, and 2) of row 1 in the zeroth view 410 are aggregated into a macro-detector, the next three individual detectors (detectors 3, 4, and 5) of row 1 in the zeroth view 410 remain as individual detectors, and the next three individual detectors (detectors 6, 7, and 8) of row 1 in the zeroth view 410 are aggregated into a macro-detector. In this way, the individual detectors of row 0 are adjacent to macro-detectors in row 1, while the macro-detector(s) of row 0 are adjacent to individual detectors in row 1. This alternating pattern continues through rows 2 and 3 of the detector array 505. Thus, detector array 505 comprises a combination of macro-detectors (depicted as shaded entries in the table 500) and individual detectors (depicted as unshaded entries in the table 500), while the distribution 512 of energy bins distributes m energy bins to the individual detectors and M energy bins to the macro-detectors, where m equals one and M equals three in the depicted example.

Furthermore, the distribution 522 of energy bins among macro-detectors and individual detectors for the first view 420 is shifted from the distribution 512 of energy bins among macro-detectors and individual detectors for the zeroth view 410. Specifically, the first three individual detectors (detectors 0, 1, and 2) of row 0 for the first view 420 are aggregated into a macro-detector, the next three individual detectors (detectors 3, 4, and 5) of row 0 for the first view 420 remain individual detectors, and the next three individual detectors (detectors 6, 7, and 8) of row 0 for the first view 420 are aggregated into a macro-detector. Thus, the distribution of energy bins among macro-detectors and individual detectors shifts for a given detector row shifts between views, such that a position in a detector row alternates between a macro-detector and an individual detector between views. This alternating pattern is further depicted by the second distribution 532 for the second view 430 relative to the first distribution 522 of the first view 420, as well as the third distribution 542 of the third view 440 relative to the second distribution 532 of the second view 430.

Thus, the detector array of the imaging system may be configured physically according to the distributions of energy bins as depicted in FIG. 4, but the data may be recorded into a photon count dataset according to the distributions of energy bins as depicted in FIG. 5. That is, while the individual detectors may physically detect photons with m energy bins, as an illustrative example, the photon count datasets acquired during a scan may include photon counts for individual detectors with m energy bins and macro-detectors with M energy bins.

By alternating the relative positions of macro-detectors and individual detectors between detector rows in the detector array 505 as well as between views during data acquisition, there is minimal loss of information in the data compression when the dataset is up-sampled before image reconstruction.

Furthermore, in addition to shifting the position of macro-detectors between detector rows as well as between views, in some examples the distribution of energy bins themselves may also be shifted. As an illustrative and non-limiting example, FIG. 6 shows a table 600 illustrating an example distribution of energy bins for different energy levels among individual detectors and macro-detectors in a detector array 605 for a sequence of views 606 according to an embodiment. Specifically, table 600 depicts a zeroth distribution 612 for a zeroth view 610 and a first distribution 622 for a first view 620 of separate energy bins, including a first energy bin E1, a second energy bin E2, and a third energy bin E3. The energy bins E1, E2, and E3 correspond to non-overlapping ranges of photon energies which may be pre-determined or in some examples may be automatically and/or manually selected by a user.

As depicted in table 600, the energy bins may be distributed among the individual detectors such that each individual detector is configured with a single energy bin, wherein adjacent individual detectors are configured with different energy bins. As depicted in the zeroth view 610 in detector row 0, the individual detector 630 (corresponding to detector 0) is configured to detect photons with energies within the first energy bin E1, the individual detector 631 (corresponding to detector 1) is configured to detect photons with energies within the second energy bin E2, and the individual detector 632 (corresponding to detector 2) is configured to detect photons with energies within the third energy bin E3. Further, the individual detectors corresponding to detectors 3, 4, and 5 in row 0 for the zeroth view 610 are configured to detect photons with energies within the first energy bin E1, the second energy bin E2, and the third energy bin E3, respectively. As depicted, the photon counts of these individual detectors are aggregated into a single macro-detector 634 configured with all three energy bins. The individual detector 636 (corresponding to detector 6) is configured to detect photons with energies within the first energy bin E1, the individual detector 637 (corresponding to detector 7) is configured to detect photons with energies within the second energy bin E2, and the individual detector 638 (corresponding to detector 8) is configured to detect photons with energies within the third energy bin E3.

In the adjacent detector row 1 for the zeroth view 610, the distribution of energy bins are shifted such that the detector 0 element is configured with the second energy bin E2, the detector 1 element is configured with the third energy bin E3, the detector 2 element is configured with the first energy bin E1, and so on throughout the detector row 1. Further, the first three detector elements 0, 1, and 2 in row 1 of the zeroth view 610 are aggregated into a macro-detector with all three energy bins E1, E2, and E3. Similarly, the distribution of energy bins are shifted again for detector rows 2 and 3, such that the zeroth detector element is configured with the third energy bin E3 for detector row 2 and the first energy bin E1 for detector row 3.

Further, as depicted, the distribution 622 of energy bins is similarly shifted for the first view 620 relative to the distribution 612 of energy bins for the zeroth view 610. For example, the detector element 0 for row 0 of the first view 620 is configured with the second energy bin E2 rather than the first energy bin E1, while the detector element 1 for row 0 of the first view 620 is configured with the third energy bin E3 rather than the second energy bin E2, and so on for each of the detector elements of each detector row in the first view 620. Thus, the macro-detector aggregation shifts between rows and views as depicted, as well as the distribution of energy bins.

As described hereinabove with regard to FIG. 3, the photon count datasets for combination detector arrays of macro-detectors and individual detectors may be up-sampled to generate a full photon count dataset for a detector array of N individual detectors with M energy bins each. As an illustrative and non-limiting example, FIG. 7 shows a table 700 illustrating an example distribution of energy bins among individual detectors in the detector array 405 for a sequence of views after up-sampling according to an embodiment. Similar to table 400 of FIG. 4, table 700 includes columns corresponding to the plurality of individual detectors 402 as well as rows corresponding to the plurality of detector rows 404 arranged in the detector array 705. Further, table 700 depicts a plurality of energy bin distributions corresponding to the plurality of views 406, including a zeroth updated distribution 712 for the zeroth view 410, a first updated distribution 722 for the first view 420, a second updated distribution 732 for the second view 430, and a third updated distribution 742 for the third view 440.

As depicted, the detector array 705 includes N individual detectors with M energy bins each, wherein N equals thirty-six and M equals three. Thus, a full photon count dataset as described hereinabove comprises photon count data for N individual detectors with M energy bins each.

In this way, a detector array includes N individual detectors, each configured with m energy bins. Photon counts initially detected by the detector array are selectively aggregated and collected into a photon count dataset for a detector array including individual detectors configured with m energy bins each and macro-detectors configured with M energy bins each. The photon count dataset is up-sampled into a full photon count dataset for a detector array including N individual detectors, each configured with M energy bins.

A technical effect of the disclosure includes a robust data compression of photon counts during data acquisition and data up-sampling with minimal loss of information. Another technical effect of the disclosure includes the selective aggregation of data regarding detected photons during data acquisition. Yet another technical effect of the disclosure includes the transmission of a reduced dataset from a rotating portion of an imaging system to a stationary portion of the imaging system. Another technical effect of the disclosure includes the reconstruction of an image with increased image resolution and increased spectral information. Yet another technical effect of the disclosure includes the display of an image reconstructed from data with increased image resolution and increased spectral information relative to an image reconstructed from the data without the data compression and up-sampling approach described herein.

In one embodiment, a method comprises detecting, with a detector array comprising a plurality of individual detectors each configured with a first number of energy bins, photons generated by an x-ray source and attenuated by a subject to be imaged, generating a first dataset, for a virtual detector array comprising a combination of individual detectors and macro-detectors, by selectively aggregating a subset of the individual detectors into the macro-detectors with a second number of energy bins, generating a second dataset, for an augmented detector array comprising the plurality of individual detectors each configured with the second number of energy bins, by up-sampling the first dataset, and reconstructing an image of the subject from the second dataset.

In a first example of the method, the virtual detector array alternates between n individual detectors configured with the first number of energy bins and a macro-detector configured with the second number of energy bins, and selectively aggregating the subset of individual detectors into the macro-detectors comprises aggregating n adjacent individual detectors into the macro-detector. In a second example of the method optionally including the first example, the virtual detector array includes a plurality of detector rows, the virtual detector array alternates between n individual detectors and the macro-detector in a detector row of the plurality of detector rows, and the virtual detector array further alternates between an individual detector and a macro-detector in a first position of each detector row. In a third example of the method optionally including one or more of the first and second examples, the method further comprises alternating positions of individual detectors and macro-detectors in the virtual detector array from view to view for the first dataset. In a fourth example of the method optionally including one or more of the first through third examples, up-sampling the first dataset to generate the second dataset comprises applying guided bi-linear interpolation to the first dataset. In a fifth example of the method optionally including one or more of the first through fourth examples, up-sampling the first dataset to generate the second dataset comprises inputting the first dataset to a trained deep learning model for generating the second dataset. In a sixth example of the method optionally including one or more of the first through fifth examples, the first number of energy bins comprises one, and wherein the second number of energy bins comprises two. In a seventh example of the method optionally including one or more of the first through fifth examples, the first number of energy bins comprises one, and wherein the second number of energy bins comprises three. In an eighth example of the method optionally including one or more of the first through seventh examples, the method further comprises generating, with the x-ray source, the photons at different energy levels corresponding to the second number of energy bins. In a ninth example of the method optionally including one or more of the first through eighth examples, the method further comprises alternating a distribution of energy bins between detector rows of the detector array and between views.

In another embodiment, a method for an imaging system comprises: controlling an x-ray source to generate a beam of x-rays towards a subject; detecting the beam of x-rays with N individual detectors arranged in a detector array, each individual detector configured with m energy bins; generating a photon count dataset alternating between a macro-detector with M energy bins and n individual detectors in each detector row, wherein M equals n times m, wherein photon counts from n adjacent individual detectors in a detector row are aggregated into the macro-detector, and wherein macro-detectors are adjacent to individual detectors in adjacent detector rows; generating a full photon count dataset including photon counts for N individual detectors each configured with M energy bins by up-sampling the photon count dataset; and reconstructing an image from the full photon count dataset.

In a first example of the method, the method further comprises controlling a gantry to rotate the x-ray source and the detector array around the subject through a plurality of views, and generating the photon count dataset for each view of the plurality of views, wherein the photon count dataset alternates positions of macro-detectors and individual detectors from view to view. In a second example of the method optionally including the first example, the method further comprises generating a collated photon count dataset from photon count datasets for all views of the plurality of views, and generating the full photon count dataset by up-sampling the collated photon count dataset. In a third example of the method optionally including one or more of the first and second examples, the method further comprises transmitting the photon count dataset for each view from a data acquisition system, the data acquisition system rotating with the gantry through the plurality of views, to a stationary computing device of the imaging system. In a fourth example of the method optionally including one or more of the first through third examples, up-sampling the first dataset comprises one of applying guided bi-linear interpolation to the first dataset or inputting the first dataset to a trained deep learning model.

In yet another embodiment, a system comprises: an x-ray source that emits a beam of x-rays toward a subject to be imaged; a detector array configured to receive the x-rays attenuated by the subject, the detector array comprising a plurality of individual detectors arranged into a plurality of detector rows; a data acquisition system (DAS) operably connected to the detector array, the DAS configured to, for each individual detector of the plurality of individual detectors, count detected photons within m energy bins, the DAS further configured to aggregate counts from n adjacent individual detectors into a macro-detector configured with M energy bins, wherein M equals m times n; and a computing device operably connected to the DAS and configured with executable instructions in non-transitory memory that when executed cause the computing device to: during a scan of the subject, control the DAS to acquire a first dataset alternating between the macro-detector and n individual detectors in each detector row; generate a second dataset by up-sampling the first dataset to include M energy bins for each individual detector of the detector array; and reconstruct an image of the subject from the second dataset.

In a first example of the system, the system further comprises a gantry defining an opening through which the subject is positioned, wherein the x-ray source and the detector array are positioned opposite each other on the gantry, and wherein the computing device is further configured with executable instructions that when executed cause the computing device to: during the scan, control the gantry to rotate through a plurality of views around the subject; control the DAS to acquire the first dataset for each view of the plurality of views; receive the first dataset from the DAS for each view of the plurality of views; collate the first dataset for each view into a collated first dataset; and generate the second dataset from the collated first dataset. In a second example of the system optionally including the first example, the DAS alternates positions of macro-detectors and individual detectors in a virtual detector array for generating the first dataset between each view of the plurality of views. In a third example of the system optionally including one or more of the first and second examples, the first dataset further alternates between macro-detectors and n individual detectors between detector rows. In a fourth example of the system optionally including one or more of the first through third examples, the system further comprises a display device communicatively coupled to the computing device, wherein the computing device is further configured with executable instructions that when executed cause the computing device to output the image to the display device for display.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields.

The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   detecting, with a detector array comprising a plurality of individual detectors each configured with a first number of energy bins, photons generated by an x-ray source and attenuated by a subject to be imaged;
   generating a first dataset, for a virtual detector array comprising a combination of individual detectors and macro-detectors, by selectively aggregating a subset of the individual detectors into the macro-detectors with a second number of energy bins;
   generating a second dataset, for an augmented detector array comprising the plurality of individual detectors each configured with the second number of energy bins, by up-sampling the first dataset; and
   reconstructing an image of the subject from the second dataset.

2. The method of claim 1, wherein the virtual detector array alternates between n individual detectors configured with the first number of energy bins and a macro-detector configured with the second number of energy bins, and wherein selectively aggregating the subset of individual detectors into the macro-detectors comprises aggregating n adjacent individual detectors into the macro-detector.

3. The method of claim 2, wherein the virtual detector array includes a plurality of detector rows, wherein the virtual detector array alternates between n individual detectors and the macro-detector in a detector row of the plurality of detector rows, wherein the virtual detector array further alternates between an individual detector and a macro-detector in a first position of each detector row.

4. The method of claim 2, further comprising alternating positions of individual detectors and macro-detectors in the virtual detector array from view to view for the first dataset.

5. The method of claim 1, wherein up-sampling the first dataset to generate the second dataset comprises applying guided bi-linear interpolation to the first dataset.

6. The method of claim 1, wherein up-sampling the first dataset to generate the second dataset comprises inputting the first dataset to a trained deep learning model for generating the second dataset.

7. The method of claim 1, wherein the first number of energy bins comprises one, and wherein the second number of energy bins comprises two.

8. The method of claim 1, wherein the first number of energy bins comprises one, and wherein the second number of energy bins comprises three.

9. The method of claim 1, further comprising generating, with the x-ray source, the photons at different energy levels corresponding to the second number of energy bins.

10. The method of claim 1, further comprising alternating a distribution of energy bins between detector rows of the detector array and between views.

11. A method for an imaging system, comprising:
    controlling an x-ray source to generate a beam of x-rays towards a subject;
    detecting the beam of x-rays with N individual detectors arranged in a detector array, each individual detector configured with m energy bins;
    generating a photon count dataset alternating between a macro-detector with M energy bins and n individual detectors in each detector row, wherein photon counts from n adjacent individual detectors in a detector row are aggregated into the macro-detector, and wherein macro-detectors are adjacent to individual detectors in adjacent detector rows;
    generating a full photon count dataset including photon counts for N individual detectors each configured with M energy bins by up-sampling the photon count dataset; and
    reconstructing an image from the full photon count dataset.

12. The method of claim 11, further comprising controlling a gantry to rotate the x-ray source and the detector array around the subject through a plurality of views, and generating the photon count dataset for each view of the plurality of views, wherein the photon count dataset alternates positions of macro-detectors and individual detectors from view to view.

13. The method of claim 12, further comprising generating a collated photon count dataset from photon count datasets for all views of the plurality of views, and generating the full photon count dataset by up-sampling the collated photon count dataset.

14. The method of claim 12, further comprising transmitting the photon count dataset for each view from a data acquisition system, the data acquisition system rotating with the gantry through the plurality of views, to a stationary computing device of the imaging system.

15. The method of claim 11, wherein up-sampling the first dataset comprises one of applying guided bi-linear interpolation to the first dataset or inputting the first dataset to a trained deep learning model.

16. A system, comprising:
    an x-ray source that emits a beam of x-rays toward a subject to be imaged;
    a detector array configured to receive the x-rays attenuated by the subject, the detector array comprising a plurality of individual detectors arranged into a plurality of detector rows;
    a data acquisition system (DAS) operably connected to the detector array, the DAS configured to, for each individual detector of the plurality of individual detectors, count detected photons within m energy bins, the DAS further configured to aggregate counts from n adjacent individual detectors into a macro-detector configured with M energy bins, wherein M equals m times n; and
    a computing device operably connected to the DAS and configured with executable instructions in non-transitory memory that when executed cause the computing device to:
       during a scan of the subject, control the DAS to acquire a first dataset alternating between the macro-detector and n individual detectors in each detector row;
       generate a second dataset by up-sampling the first dataset to include M energy bins for each individual detector of the detector array; and
       reconstruct an image of the subject from the second dataset.

17. The system of claim 16, further comprising a gantry defining an opening through which the subject is positioned, wherein the x-ray source and the detector array are positioned opposite each other on the gantry, and wherein the computing device is further configured with executable instructions that when executed cause the computing device to:
- during the scan, control the gantry to rotate through a plurality of views around the subject;
- control the DAS to acquire the first dataset for each view of the plurality of views;
- receive the first dataset from the DAS for each view of the plurality of views;
- collate the first dataset for each view into a collated first dataset; and
- generate the second dataset from the collated first dataset.

18. The system of claim 17, wherein the DAS alternates positions of macro-detectors and individual detectors in a virtual detector array for generating the first dataset between each view of the plurality of views.

19. The system of claim 16, wherein the first dataset further alternates between macro-detectors and n individual detectors between detector rows.

20. The system of claim 16, further comprising a display device communicatively coupled to the computing device, wherein the computing device is further configured with executable instructions that when executed cause the computing device to output the image to the display device for display.

* * * * *